(12) United States Patent
Williams et al.

(10) Patent No.: US 9,962,514 B2
(45) Date of Patent: May 8, 2018

(54) VENTILATOR FLOW VALVE

(71) Applicant: CareFusion 303, Inc., San Diego, CA (US)

(72) Inventors: Malcolm R. Williams, San Clemente, CA (US); Adrian D. DeSilva, Riverside, CA (US); Huy Thanh Vu, Westminster, CA (US)

(73) Assignee: VYAIRE MEDICAL CAPITAL LLC, Yorba Linda, CA (US)

( * ) Notice: Subject to any disclaimer, the term of this patent is extended or adjusted under 35 U.S.C. 154(b) by 885 days.

(21) Appl. No.: 14/318,274

(22) Filed: Jun. 27, 2014

(65) Prior Publication Data
US 2015/0000663 A1 Jan. 1, 2015

Related U.S. Application Data

(63) Continuation-in-part of application No. 13/931,418, filed on Jun. 28, 2013, now Pat. No. 9,433,743.

(51) Int. Cl.
*F16K 31/06* (2006.01)
*A61M 16/20* (2006.01)
*A61M 16/00* (2006.01)

(52) U.S. Cl.
CPC ...... *A61M 16/202* (2014.02); *A61M 16/0051* (2013.01); *A61M 16/0066* (2013.01);
(Continued)

(58) Field of Classification Search
CPC .......... A61M 16/0066; A61M 16/0051; A61M 16/20; A61M 16/202; A61M 16/203; A61M 16/204; A61M 16/205; A61M 2205/125; A61M 2205/128; A61M 2205/505; A61M 2205/581; A61M 2205/3317; A61M 2016/0027; A61M 2016/003;
(Continued)

(56) References Cited

U.S. PATENT DOCUMENTS

| 2,037,880 A | 4/1936 | Charavay |
| 2,510,125 A | 6/1950 | Meakin |

(Continued)

FOREIGN PATENT DOCUMENTS

| CN | 1041204 A | 4/1990 |
| CN | 101225881 A | 7/2008 |

(Continued)

OTHER PUBLICATIONS

International Search Report and Written Opinion in PCT Application No. PCT/US2014/044438 dated Oct. 28, 2014, 11 pages.
(Continued)

*Primary Examiner* — Ian Paquette
(74) *Attorney, Agent, or Firm* — McDermott Will & Emery LLP

(57) ABSTRACT

Described herein is a flow control valve for a ventilator that controls gas flow through a patient line in response to a target pressure within the line. The valve controls gas flow by (i) providing both a high frequency signal and a low frequency signal through a coil positioned in a fixed magnetic field, (ii) determining a position of the coil by detecting the high frequency signal, and (iii) controlling a position of the coil by adjusting the low frequency signal based on the determined position and/or velocity of the coil.

18 Claims, 9 Drawing Sheets

(52) U.S. Cl.
CPC ........ *A61M 16/024* (2017.08); *A61M 16/204* (2014.02); *A61M 16/205* (2014.02); *F16K 31/0655* (2013.01); *F16K 31/0675* (2013.01); *A61M 2016/003* (2013.01); *A61M 2016/0027* (2013.01); *A61M 2016/0039* (2013.01); *A61M 2016/0042* (2013.01); *A61M 2205/125* (2013.01); *A61M 2205/128* (2013.01); *A61M 2205/3317* (2013.01); *A61M 2205/505* (2013.01); *A61M 2205/581* (2013.01)

(58) Field of Classification Search
CPC ..... A61M 2016/039; A61M 2016/0042; F16K 31/802; F16K 31/0655; F16K 31/082; F16K 31/0675; F16K 31/0679
See application file for complete search history.

(56) References Cited

U.S. PATENT DOCUMENTS

| | | |
|---|---|---|
| 2,634,311 A | 4/1953 | Darling |
| 3,140,042 A | 7/1964 | Fujii |
| 3,673,541 A | 6/1972 | Volinskie |
| 3,776,215 A | 12/1973 | Howard et al. |
| 3,788,765 A | 1/1974 | Rusak |
| 4,167,369 A | 9/1979 | Ishihara |
| 4,243,357 A | 1/1981 | Flynn et al. |
| 4,381,668 A | 5/1983 | Sato et al. |
| 4,543,041 A | 9/1985 | French et al. |
| 4,562,744 A | 1/1986 | Hall et al. |
| 4,571,801 A | 2/1986 | Ewing |
| 4,649,760 A | 3/1987 | Wedding |
| 4,754,651 A | 7/1988 | Shortridge et al. |
| 4,763,645 A | 8/1988 | Kapp |
| 4,809,742 A | 3/1989 | Grau |
| 4,825,904 A | 5/1989 | Grau et al. |
| 4,909,545 A | 3/1990 | Hohol |
| 4,978,281 A | 12/1990 | Conger, IV |
| 5,064,346 A | 11/1991 | Atarashi et al. |
| 5,127,400 A | 7/1992 | DeVries et al. |
| 5,190,068 A | 3/1993 | Philbin |
| 5,207,239 A * | 5/1993 | Schwitalla ......... B60G 17/0195 137/870 |
| 5,265,594 A | 11/1993 | Olsson et al. |
| 5,277,196 A | 1/1994 | Hankinson et al. |
| 5,295,397 A | 3/1994 | Hall et al. |
| 5,331,995 A | 7/1994 | Westfall et al. |
| 5,339,807 A | 8/1994 | Carter |
| 5,365,795 A | 11/1994 | Brower, Jr. |
| 5,461,932 A | 10/1995 | Hall et al. |
| 5,478,206 A | 12/1995 | Prahst |
| 5,537,992 A | 7/1996 | Bjoernstijerna et al. |
| 5,572,992 A | 11/1996 | Kankkunen et al. |
| 5,604,681 A | 2/1997 | Koeninger |
| 5,606,236 A | 2/1997 | Tennies et al. |
| 5,771,884 A | 6/1998 | Yarnall et al. |
| 5,918,596 A | 7/1999 | Heinonen |
| 5,954,051 A | 9/1999 | Heinonen et al. |
| 6,017,315 A | 1/2000 | Starr et al. |
| 6,139,262 A | 10/2000 | Ravidranath |
| 6,151,557 A | 11/2000 | Broden et al. |
| 6,422,092 B1 | 7/2002 | Morrison et al. |
| 6,422,256 B1 | 7/2002 | Balazy et al. |
| 6,553,923 B2 | 4/2003 | Gatley, Jr. |
| 6,578,818 B1 | 6/2003 | Krimmer et al. |
| 6,609,431 B1 | 8/2003 | Tietsworth et al. |
| 6,622,724 B1 | 9/2003 | Truitt et al. |
| 6,820,620 B2 | 11/2004 | Rochat |
| 6,945,123 B1 | 9/2005 | Kuehl et al. |
| 7,107,834 B2 | 9/2006 | Meneghini et al. |
| 7,121,139 B2 | 10/2006 | Shajii et al. |
| 7,636,640 B2 | 12/2009 | Wang et al. |
| 7,819,022 B2 | 10/2010 | Hope |
| 7,826,986 B2 | 11/2010 | McDonald |
| 8,504,318 B2 | 8/2013 | Mendelson et al. |
| 9,003,877 B2 | 4/2015 | Qasimi et al. |
| 2002/0085952 A1 | 7/2002 | Ellingboe et al. |
| 2002/0198668 A1 | 12/2002 | Lull et al. |
| 2003/0106554 A1 | 6/2003 | de Silva et al. |
| 2003/0220605 A1 | 11/2003 | Bowman et al. |
| 2004/0074311 A1 | 4/2004 | Lull et al. |
| 2004/0177703 A1 | 9/2004 | Schumacher et al. |
| 2004/0187871 A1 | 9/2004 | Kimmel et al. |
| 2005/0004534 A1 | 1/2005 | Lockwood et al. |
| 2005/0241412 A1 | 11/2005 | Tison et al. |
| 2006/0079765 A1 | 4/2006 | Neer et al. |
| 2006/0144163 A1 | 7/2006 | Friberg |
| 2006/0162466 A1 | 7/2006 | Wargo et al. |
| 2006/0236781 A1 | 10/2006 | Ohmi et al. |
| 2007/0193369 A1 | 8/2007 | Evans et al. |
| 2007/0265877 A1 | 11/2007 | Rice et al. |
| 2007/0277824 A1 | 12/2007 | Aylsworth et al. |
| 2008/0059084 A1 | 3/2008 | Wang et al. |
| 2008/0092891 A1 | 4/2008 | Cewers |
| 2008/0105259 A1 | 5/2008 | de Silva et al. |
| 2008/0283062 A1 | 11/2008 | Esposito, Jr. |
| 2009/0038615 A1 | 2/2009 | Bradley |
| 2009/0093774 A1 | 4/2009 | Wang et al. |
| 2009/0095068 A1 | 4/2009 | Redemann et al. |
| 2009/0113996 A1 | 5/2009 | Wang et al. |
| 2009/0293634 A1 | 12/2009 | Ong |
| 2009/0326839 A1 | 12/2009 | Rogers et al. |
| 2010/0031737 A1 | 2/2010 | Saito et al. |
| 2010/0139660 A1 | 6/2010 | Adahan |
| 2010/0229967 A1 | 9/2010 | Yasuda et al. |
| 2010/0236552 A1 | 9/2010 | Kwok et al. |
| 2010/0307490 A1 | 12/2010 | Broborg et al. |
| 2011/0100364 A1 | 5/2011 | Faram |
| 2011/0126834 A1 | 6/2011 | Winter et al. |
| 2011/0126837 A1 | 6/2011 | Winter et al. |
| 2011/0301867 A1 | 12/2011 | Davis et al. |
| 2012/0065533 A1 | 3/2012 | Carrillo, Jr. et al. |
| 2012/0085349 A1 | 4/2012 | Tobias et al. |
| 2012/0185102 A1 | 7/2012 | Skoglund et al. |
| 2012/0204874 A1 | 8/2012 | Sofranko |
| 2012/0226449 A1 | 9/2012 | Delache et al. |
| 2012/0229272 A1 | 9/2012 | Jacob et al. |
| 2012/0285454 A1 | 11/2012 | Nibu et al. |
| 2012/0285455 A1 | 11/2012 | Varga et al. |
| 2012/0318383 A1 | 12/2012 | Yasuda et al. |
| 2013/0036806 A1 | 2/2013 | Kohno |
| 2013/0079667 A1 | 3/2013 | Berkcan et al. |
| 2013/0153040 A1 | 6/2013 | Goto et al. |
| 2013/0220314 A1 | 8/2013 | Bottom |
| 2013/0247905 A1 | 9/2013 | Miller et al. |
| 2014/0054479 A1 | 2/2014 | Shen |
| 2014/0066880 A1 | 3/2014 | Prince et al. |
| 2014/0182590 A1 | 7/2014 | Platt et al. |
| 2014/0251322 A1 | 9/2014 | Miller |
| 2014/0326242 A1 * | 11/2014 | Ahmad ............. A61M 16/0045 128/204.23 |
| 2015/0020807 A1 | 1/2015 | Kimmel |
| 2015/0096560 A1 | 4/2015 | Klenner et al. |
| 2015/0143921 A1 | 5/2015 | Postberg et al. |
| 2016/0256646 A1 | 9/2016 | Vazales |

FOREIGN PATENT DOCUMENTS

| | | |
|---|---|---|
| CN | 101687086 A | 3/2010 |
| CN | 102155570 A | 8/2011 |
| CN | 202366282 U | 8/2012 |
| CN | 102686888 A | 9/2012 |
| CN | 102927292 A | 2/2013 |
| CN | 103041492 A | 4/2013 |
| CN | 202870631 U | 4/2013 |
| EP | 0829793 A1 | 3/1998 |
| EP | 1127583 A2 | 8/2001 |
| EP | 1658874 A2 | 5/2006 |
| EP | 2402616 A1 | 1/2012 |
| JP | 556597 A | 1/1981 |
| WO | WO-0138832 A2 | 5/2001 |
| WO | WO-2006024532 A1 | 3/2006 |

(56) References Cited

FOREIGN PATENT DOCUMENTS

| WO | WO-2011055254 A1 | 5/2011 |
|---|---|---|
| WO | WO-2013002699 A1 | 1/2013 |
| WO | WO-2013080079 A1 | 6/2013 |

OTHER PUBLICATIONS

International Search Report and Written Opinion in PCT Application No. PCT/US2014/044441 dated Oct. 31, 2014, 12 pages.
Invitation to Pay Additional Fees in PCT Application No. PCT/US2014/044743 dated Oct. 21, 2014, 7 pages.
International Search Report and Written Opinion in PCT Application No. PCT/US210/044442 dated Nov. 3, 2014, 10 pages.
International Search Report and Written Opinion for International Application No. PCT/US2014/044737, dated May 19, 2015, 18 pages.
Chinese Office Action for Application No. 201480036971.X, dated Oct. 8, 2016, 10 pages excluding English translation.
Chinese Office Action for Application No. 201480037104.8, dated Nov. 17, 2016, 5 pages excluding English translation.
International Search Report and Written Opinion for Application No. PCT/US2015/038157, dated Nov. 5, 2015, 12 pages.
Chinese Office Action for Application No. 201480037090.X, dated Sep. 26, 2016, 6 pages excluding English translation.
International Search Report and Written Opinion for Application No. PCT/US2015/038155, dated Dec. 17, 2015, 18 pages.
Invitation to Pay Additional Fees and Partial Search Report for Application No. PCT/US2015/038155, dated Oct. 7, 2015, 7 pages.
Chinese Office Action for Application No. 201480036606.9, dated Sep. 2, 2016, 6 pages excluding translation.
Invitation to Pay Additional Fees in International Application No. PCT/US2014/044737 dated Oct. 28, 2014, 7 pages.
International Search Report for International Application No. PCT/US2014/044743, dated Jan. 22, 2015, 6 pages.
International Search Report and Written Opinion in PCT Application No. PCT/US2014/044724 dated Oct. 21, 2014, 12 pages.
Australian Examination Report No. 1 for Application No. 2014302094, dated Feb. 14, 2018, 3 pages.
Fehr, R., "The Basics of Inductance", Feb. 1, 2003, EC&M.

* cited by examiner

VENTILATOR FLOW VALVE

CROSS-REFERENCES TO RELATED APPLICATIONS

This application is a continuation-in-part application of U.S. patent application Ser. No. 13/931,418, entitled "VENTILATOR EXHALATION FLOW VALVE," filed Jun. 28, 2013, the entire content of which is incorporated herein by reference.

BACKGROUND

Field

The present disclosure generally relates to ventilation systems and, in particular, to a ventilator flow valve.

Description of the Related Art

Patients with respiratory injury, such as chronic respiratory failure, may be provided with a ventilator to assist with their breathing or, in severe cases, take over the breathing function entirely. Ventilators typically provide a flow of air, or other breathing gases, at an elevated pressure during an inhalation interval, followed by an exhalation interval where the pressurized air is diverted so that the air within the patient's lungs can be naturally expelled. The inhalation interval may be initiated upon detection of a patient's natural inhalation or by the ventilator.

Ventilators are available in a variety of sizes with different ranges of air flows and pressures that can be provided. For example, a neonatal patient will require a much lower pressure and volume of air per breath than an adult.

SUMMARY

Described herein are ventilators having a valve that is a software-controlled valve used to adjust the flow of gas passing through a port of the ventilator. The valve is controlled by a software control signal and works in conjunction with a ventilator's gas delivery subsystems to maintain user set pressure control levels. In continuous positive airway pressure ("CPAP") therapy, the valve preferably helps maintain a set pressure.

Described herein are ventilators having an exhalation valve that is a software-controlled valve used to adjust the flow of gas passing through an expiratory port of the ventilator to the outside environment. The exhalation valve is controlled by a software control signal and works in conjunction with a ventilator's gas delivery subsystems to maintain user set pressure control levels. In CPAP therapy, the exhalation valve preferably maintains a set pressure, and outlet flow is controlled at a specified target bias flow rate. Additional (demand) flow is provided to maintain the pressure in the event of patient inspiratory flow exceeding the bias flow.

Some implementations described herein relate to a flow control device comprising a high frequency source configured to generate a high frequency signal, a low frequency source configured to generate a low frequency signal, and a fixed magnetic field. The flow control device further comprises a drive coil configured to move within the fixed magnetic field in response to the low frequency signal and configured to receive the high frequency signal, and a detection coil adjacent the drive coil and configured to detect the high frequency signal in the drive coil. The detected high frequency signal corresponds to a position of the drive coil. The flow control device further comprises a processor coupled to the high frequency source and the low frequency source and configured to receive the detected high frequency signal from the detection coil. The flow control device further comprises a seal configured to move based on the position of the drive coil, and a valve orifice defining a valve seat and a variable opening. The variable opening is adjustable based on a position of the seal relative to the valve seat.

Described herein are ventilator systems that include, for example, a first valve connected to a supply channel. The first valve comprises a first high frequency source configured to generate a first high frequency signal, a first low frequency source configured to generate a first low frequency signal, and a first fixed magnetic field. The first valve further comprises a first drive coil configured to move within the first fixed magnetic field in response to the first low frequency signal and configured to receive the first high frequency signal, and a first detection coil adjacent the first drive coil and configured to detect the first high frequency signal in the drive coil. The detected first high frequency signal corresponds to a position of the first drive coil. The first valve further comprises a first processor coupled to the first high frequency source and the first low frequency source and configured to receive the detected first high frequency signal from the first detection coil. The first valve further comprises a first seal configured to move based on the position of the first drive coil, and a variable first valve orifice defining a first valve seat. The first valve orifice is adjustable based on a position of the first seal relative to the first valve seat.

Described herein are also methods for adjusting pressure in a ventilator line. Some methods include sending a high frequency signal and a low frequency signal to a drive coil. The low frequency signal causes the drive coil to move within a fixed magnetic field, and the drive coil causes a seal to adjust a variable valve orifice of the valve. The methods also include detecting the high frequency signal in the drive coil, determining a velocity of the drive coil based on the detected high frequency signal, and modifying the low frequency signal based on the determined velocity of the drive coil.

Some embodiments described herein relate to a valve that includes a valve orifice with an adjustable opening; a fixed magnetic field; a force coil configured to be moved within the fixed magnetic field in response to a low frequency current; a current amplifier configured to direct a summed low frequency current and a high frequency current into the force coil; a feedback coil configured to detect the high frequency current in the force coil, the detected high frequency current having a magnitude that is proportional to a force coil position within the fixed magnetic field. The valve can also include a processor configured (i) to receive data relating to the position of the force coil and (ii) to send instructions to the current amplifier; and a diaphragm configured to adjust the valve orifice opening based on the position of the force coil.

Described herein are ventilator systems that include, for example, a gas source configured to provide a gas to a patient via a supply channel; an exhaust channel configured to direct exhaust gas from the patient; and an exhaust valve. The exhaust valve may include a force coil configured to be moved within a fixed magnetic field in response to a low frequency current; a current amplifier configured to direct a summed low frequency current and a high frequency current into the force coil; a feedback coil configured to detect the high frequency current in the force coil; a processor configured (i) to receive data relating to the position of the force coil, (ii) to receive data relating to pressure within the exhaust channel, and (iii) to send instructions to the current amplifier based on the position of the coil and the pressure; and a diaphragm configured to adjust opening of a valve orifice based on the instructions from the processor.

Described herein are also methods for adjusting pressure in a ventilator line. Some methods include the following steps: directing a summed low frequency current and a high frequency current from a current amplifier into a force coil that is configured (i) to be moved within a fixed magnetic field in response to the low frequency current and (ii) to control a diaphragm to adjust opening of a valve orifice; detecting the high frequency current in the force coil, the detected high frequency current having a magnitude that is proportional to a position of the force coil within the fixed magnetic field; detecting the pressure in the ventilator line; and changing the low frequency current to move the force coil within the fixed magnetic field, thereby adjusting the opening of a valve orifice, in response to the detected pressure.

For purposes of summarizing the disclosure, certain aspects, advantages, and novel features of the disclosure have been described. It is to be understood that not necessarily all such advantages may be achieved in accordance with any particular embodiment of the disclosure. Thus, the disclosure may be embodied or carried out in a manner that achieves or optimizes one advantage or group of advantages as taught herein without necessarily achieving other advantages taught or suggested.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

Figure 1:
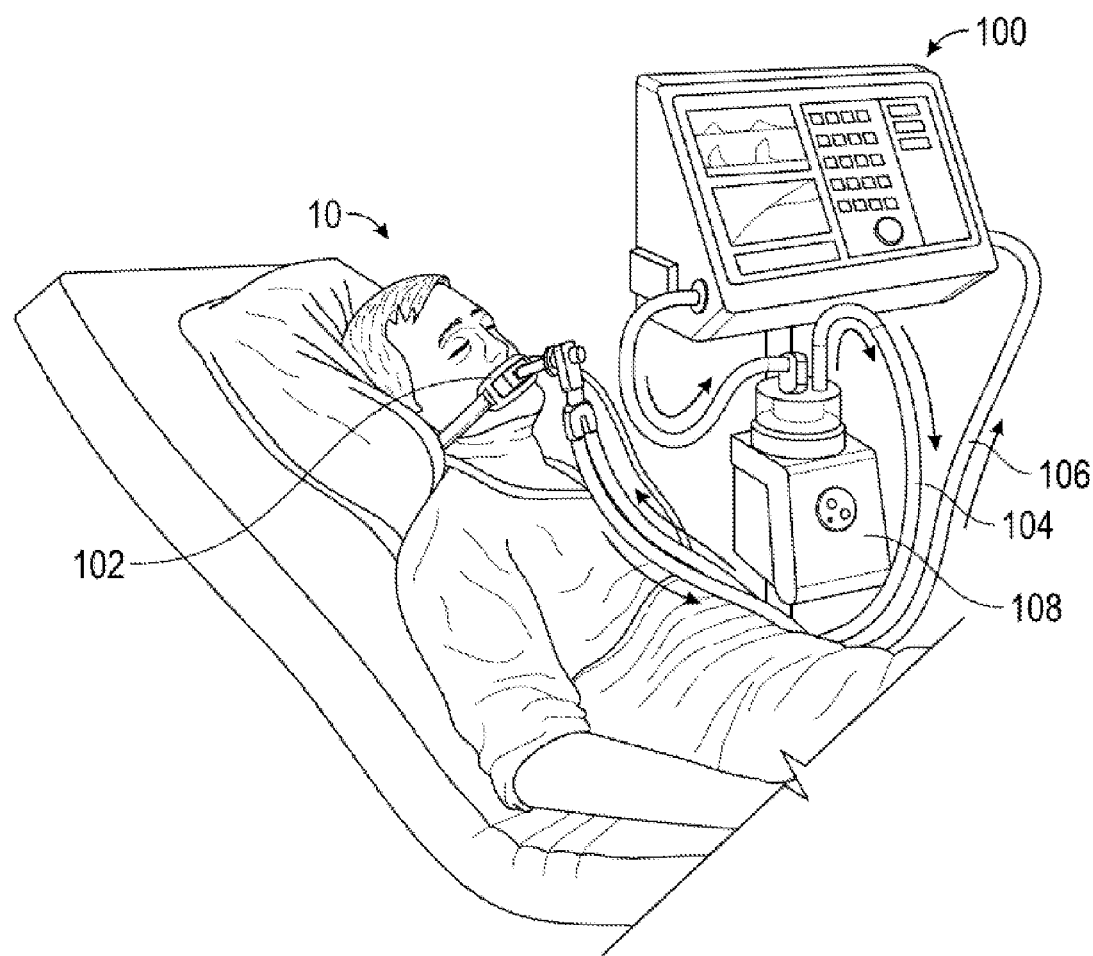
FIG. 1 depicts a patient using an exemplary ventilation system according to certain aspects of the present disclosure.

In the following detailed description, numerous specific details are set forth to provide a full understanding of the present disclosure. It will be apparent, however, to one ordinarily skilled in the art that embodiments of the present disclosure may be practiced without some of the specific details. In other instances, well-known structures and techniques have not been shown in detail so as not to obscure the disclosure. In the referenced drawings, like numbered elements are the same or essentially similar. Reference numbers may have letter suffixes appended to indicate separate instances of a common element while being referred to generically by the same number without a suffix letter.

While the discussion herein is directed to a ventilator for use in a hospital, the disclosed concepts and methods may be applied to environments, such as a home or long-term care facility, and other fields, such as deep-sea diving, that would benefit from accurate flow measurement of a variety of gas mixtures. Those of skill in the art will recognize that these same features and aspects may also be applied to the sensing and control of other fluids besides medical gases.

Within this document, the term "gas" shall be interpreted to mean both a single material in gaseous form, for example oxygen, and a mixture of two or more gases, for example air or heliox (a mixture of oxygen and helium). A gas may include water or other liquids in the form of vapor or suspended droplets. A gas may also include solid particulates suspended in the gas.

Within this document, the term "pure," when used with reference to a gas, means that the gas meets commonly accepted medical standards for purity and content.

Within this document, the term "temperature sensor" means a device configured to measure temperature and to provide a signal that is related to the measured temperature. A temperature sensor may include electronics to provide a drive current or voltage and/or measure a current or voltage. The electronics may further include conditioning and conversion circuitry and/or a processor to convert the measured value to a signal that may be in analog or digital form.

Within this document, the term "pressure sensor" means a device configured to measure a gas pressure and provide a signal that is related to the measured pressure. A pressure sensor may include electronics to provide a drive current or voltage and/or measure a current or voltage. The electronics may further include conditioning and conversion circuitry and/or a processor to convert the measured value to a signal that may be in analog or digital form. The pressure may be provided in absolute terms or "gauge" pressure, i.e., relative to ambient atmospheric pressure.

Described herein are ventilators having one or more valves that are software-controlled valves. These valves may be used to adjust the flow of gas passing through a port of the ventilator and can be configured to be positioned on the exhalation side of a ventilation system (meaning in connection with system components that receive exhaled air from a patient) or on an inhalation side of a ventilation system (meaning in connection with system components that provide air to a patient). The valves can be controlled by a software control signal and work in conjunction with a ventilator's gas delivery subsystems to maintain user set pressure control levels. In CPAP therapy, an exhalation valve preferably maintains a set pressure, and outlet flow is controlled at a specified target bias flow rate. Additional (demand) flow may be provided through an inhalation valve to control the pressure.

An exhalation subsystem of a ventilator comprises an exhalation valve, an exhalation flow sensor, and a heated filter and water trap. As explained herein, the exhalation valve is a software-controlled valve that is used to adjust the flow of gas passing through the expiratory port of the ventilator to the outside environment. The exhalation valve is controlled by a software control signal and works in conjunction with a ventilator's gas delivery subsystems to maintain user set pressure control levels.

As explained herein, the exhalation valve operates on the principle of a force balance across a control diaphragm, which may be a disposable valve membrane. In some embodiments, a linear magneto-mechanical actuator controls a force on the diaphragm, which in turn controls the circuit or ventilator line pressure. The force generated by the actuator is based on a command from the software closed-loop controller.

FIG. 1 depicts a patient 10 using an exemplary ventilation system with a ventilator 100 according to certain aspects of the present disclosure. The ventilator 100 operates as a gas source for providing gas to a patient (e.g., for respiration). In this example, the ventilator system includes a supply channel, tube, or "limb" 104, a return or exhaust channel, tube, or limb 106, a conditioning module 108 that may, for example, warm or humidify the air passing through the supply limb 104. The supply and exhaust limbs 104, 106 are both coupled to a patient interface device 102 that, in this example, is a mask that fits over the mouth of the patient 10. In other embodiments (not shown in FIG. 1), the patient interface device 102 may include a nasal mask, an intubation device, or any other breathing interface device as known to those of skill in the art.

Figure 2A:
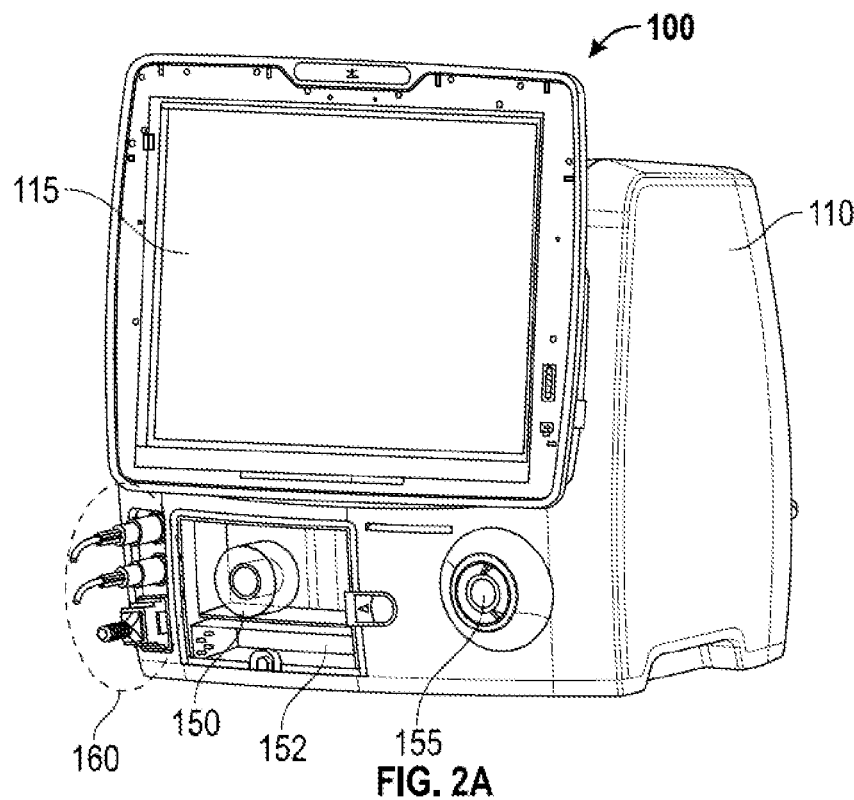
FIGS. 2A and 2B are front and rear views of an exemplary ventilator according to certain aspects of the present disclosure.
Figure 2B:
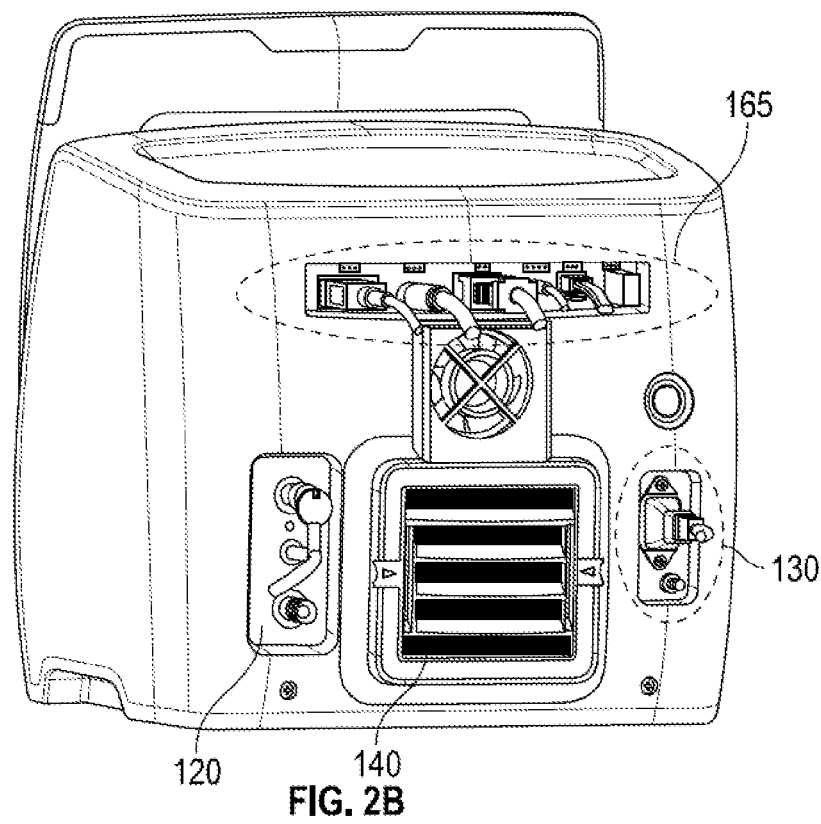

FIGS. 2A and 2B are front and rear views of the ventilator 100 according to certain aspects of the present disclosure. The ventilator 100 has a housing 110 with an attached user interface 115 that, in certain embodiments, comprises a display and a touchscreen. In FIG. 2A, it can be seen that the front of the housing 110 includes a supply port 155 for a supply limb, such as supply limb 104 in FIG. 1, and a return port 150 for an exhaust, such as exhaust limb 106 in FIG. 1. The return port 150 may be mounted over an access door 152 that provides access to a filter (not visible in FIG. 2A) that filters and absorbs moisture from the exhaled breath of the patient 10. In certain embodiments, there may also be a front connection panel 160 for connection to external instruments or a network interface cable.

FIG. 2B shows a rear view of the ventilator 100 with a gas inlet adapter 120, an air intake port 140, and a power interface 130 that may include a power plug connector and a circuit breaker reset switch. There may also be a rear interface panel 165 for connection to external instruments or a network interface cable.

Figure 3:
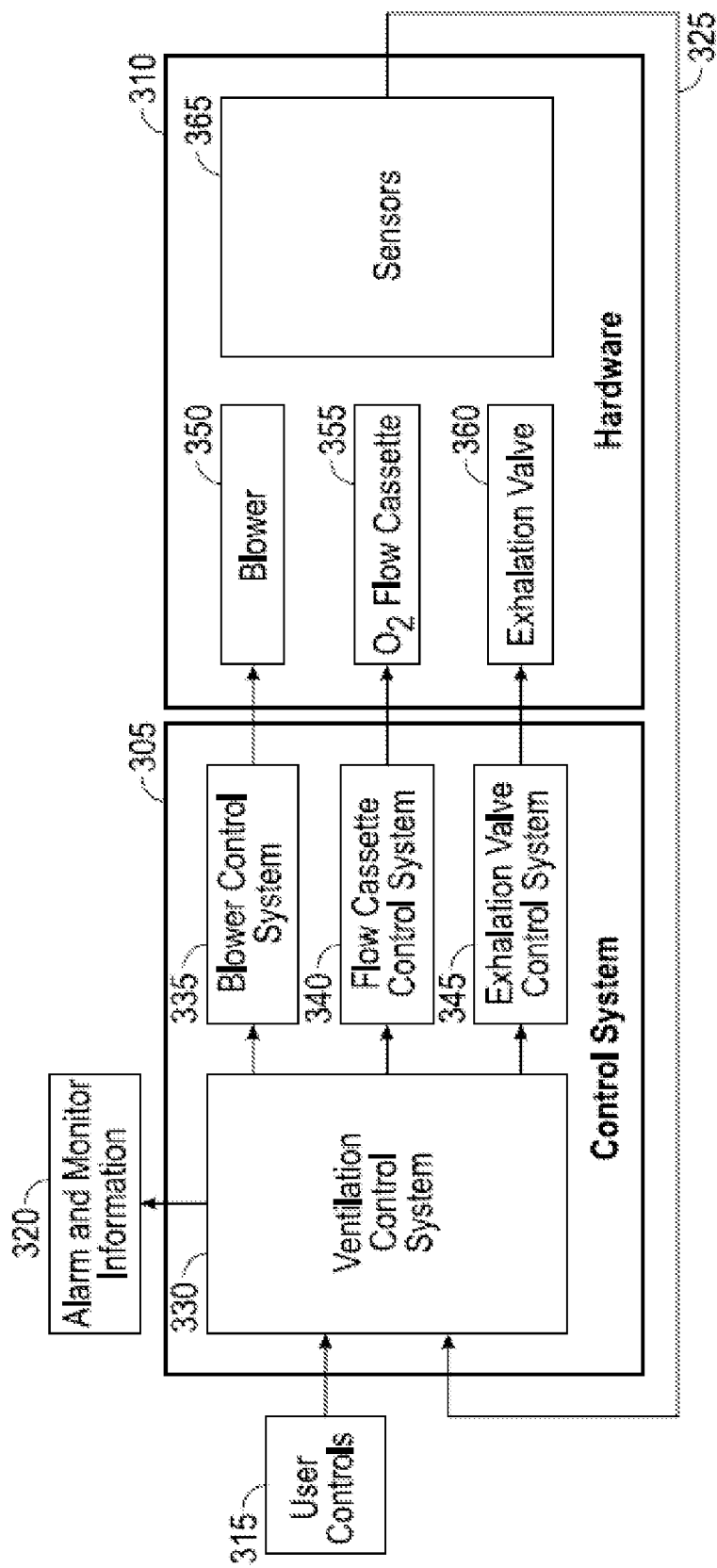
FIG. 3 is a schematic representation of a ventilator according to certain aspects of the present disclosure.

FIG. 3 illustrates a schematic depiction of the ventilator 100 having a control system 305, system hardware 310, user input 315, output 320, and feedback 325. The control system 305 includes a ventilation control system 330 that receives user input 315. The control system 305 includes hardware control systems that control respective hardware components of the ventilator 100. For example, the hardware control systems may include a blower control system 335, a flow cassette control system 340, and an exhalation valve control system 345. The blower control system 335 controls a respective blower 350, the flow cassette control system 340 controls a respective flow cassette 355, and the exhalation valve control system 345 controls a respective exhalation valve 360.

The system hardware 310 includes sensors 365 that detect information from the system hardware 310, for example, the blower 350, the flow cassette 355, and the exhalation valve 360. The sensors 365 produce one or more feedback signals 325 that are received by the ventilation control system 330. The ventilation control system 330 receives the feedback control signals 325 and the user input 315 and sends information to an output 320. The output 320 can include, for example, monitoring information and alarms.

Figure 4A:
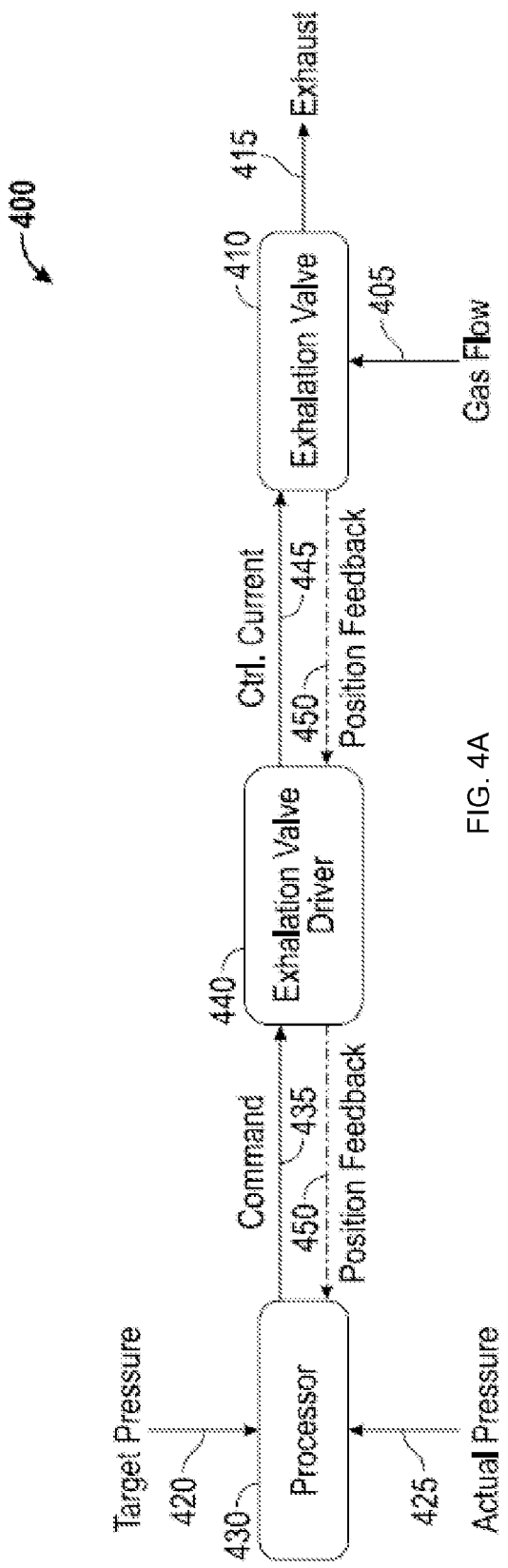
FIG. 4A is a schematic depiction of a feedback system according to certain aspects of the present disclosure.

One example of feedback and control of the ventilator 100 is depicted in FIG. 4A, which illustrates a schematic depiction of an exhalation control feedback system 400 that determines an amount of gas flow 405 that is permitted to pass through an exhalation valve 410. The illustrated embodiment of the feedback system 400 is based on a target pressure 420 and an actual circuit pressure 425 (or a pressure within a line of the ventilator 100).

As illustrated in FIG. 4A, a processor 430 receives an input signal relating to the actual circuit pressure 425 and compares the actual circuit pressure 425 to the target pressure 420. Based on this comparison, the processor 430 sends a command signal 435 to an exhalation valve driver 440. The exhalation valve driver 440 is configured to control a position of the exhalation valve 410 to regulate the gas flow 405 through the exhalation valve 410. In the illustrated embodiment, the exhalation valve driver 440 sends a control current 445 to the exhalation valve 410 to maintain or adjust the exhalation valve 410 to modify or adjust the pressure within the ventilator line.

For example, if the actual circuit pressure 425 was found to be too high, the processor 430 sends a command 435 to the exhalation valve driver 440 to open the exhalation valve 410 to reduce pressure within the ventilator line. The exhalation valve driver 440, upon receiving the command 435 to relieve pressure, adjusts the control current 445 to the exhalation valve 410 to increase the opening of the exhalation valve 410 and relieve pressure within the ventilator line. As the control current 445 increases the opening of the exhalation valve 410, the processor 430 receives position feedback 450 of the exhalation valve 410 via the exhalation valve driver 440, such that the processor 430 is able to determine the degree to which the exhalation valve 410 is open.

If the actual circuit pressure 425 input to the processor 430 was found to be too low, the processor 430 directs the driver 440 to adjust the control current 445 to the exhalation valve 410 to decrease the opening of the exhalation valve 410 such that pressure within the ventilator line is increased. If the actual circuit pressure 425 input to the processor 430 was found to be at an acceptable level or within an acceptable range, the processor 430 directs the driver 440 to maintain the control current 445 to the exhalation valve 410 to maintain the position of the exhalation valve 410.

Figure 4B:
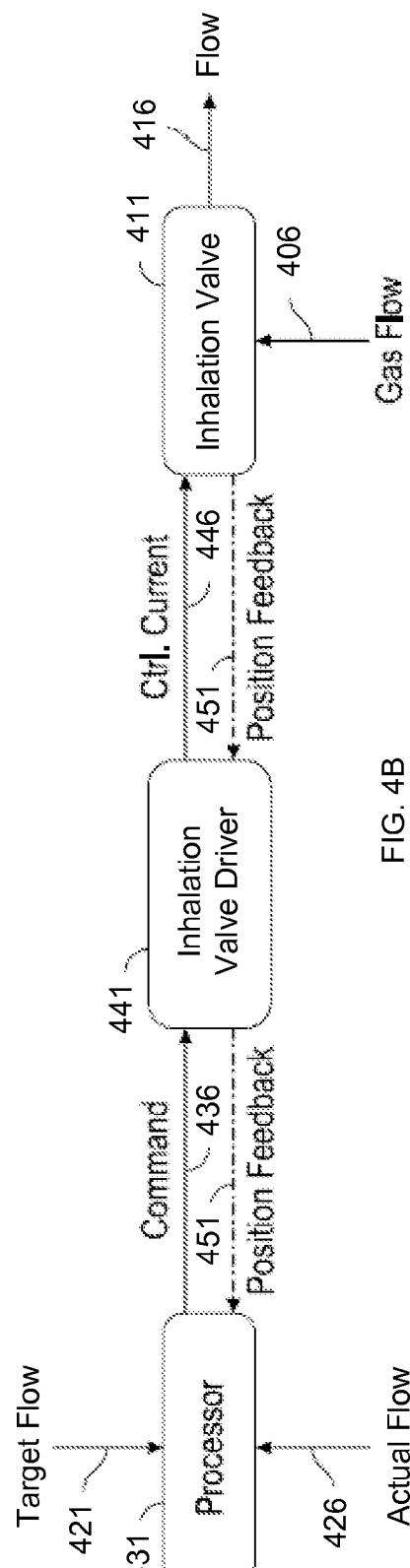
FIG. 4B is a schematic depiction of a feedback system according to certain aspects of the present disclosure.

Another example of feedback and control of the ventilator 100 is depicted in FIG. 4B, which illustrates a schematic depiction of an inhalation control feedback system 401 that determines an amount of gas flow 406 that is permitted to pass through an inhalation valve 411. The illustrated embodiment of the feedback system 401 is based on a target flow 421 and an actual flow 426 (or a flow within a line of the ventilator 100). The position feedback may be used to determine flow, using the orifice characteristics of the valve and generally understood principles of fluid flow. Multiple gas types may be controlled based on the identified gas type (or gas id). The primary advantage of this flow measurement method is that the need for a separate flow sensor is eliminated and the resulting package provides for a compact flow delivery system.

As illustrated in FIG. 4B, a processor 431 receives an input signal relating to the actual flow 426 and compares the actual flow 426 to the target flow 421. Based on this comparison, the processor 431 sends a command signal 436 to an inhalation valve driver 441. The inhalation valve driver 441 is configured to control a position of the inhalation valve 411 to regulate the gas flow 406 through the inhalation valve 411. In the illustrated embodiment, the inhalation valve driver 441 sends a control current 446 to the inhalation valve 411 to maintain or adjust the inhalation valve 411 to modify or adjust the flow rate through the ventilator line.

For example, if the actual flow 426 was found to be too high, the processor 431 sends a command 436 to the inhalation valve driver 441 to close the inhalation valve 411 to reduce the flow rate through the ventilator line. The inhalation valve driver 441, upon receiving the command 436 to reduce the flow rate, adjusts the control current 446 to the inhalation valve 411 to decrease the opening of the inhalation valve 411 and reduce the flow rate within the ventilator line. As the control current 446 decreases the opening of the inhalation valve 411, the processor 431 receives position feedback 451 of the inhalation valve 411 via the inhalation valve driver 441, such that the processor 431 is able to determine the degree to which the inhalation valve 411 is open.

If the actual flow 426 input to the processor 431 was found to be too low, the processor 431 directs the inhalation driver 441 to adjust the control current 446 to the inhalation valve 411 to increase the opening of the inhalation valve 411 such that the flow rate through the ventilator line is increased. If the actual flow 426 input to the processor 431 was found to be at an acceptable level or within an acceptable range, the processor 431 directs the driver 441 to maintain the control current 446 to the inhalation valve 411 to maintain the position of the inhalation valve 411.

Figure 5:
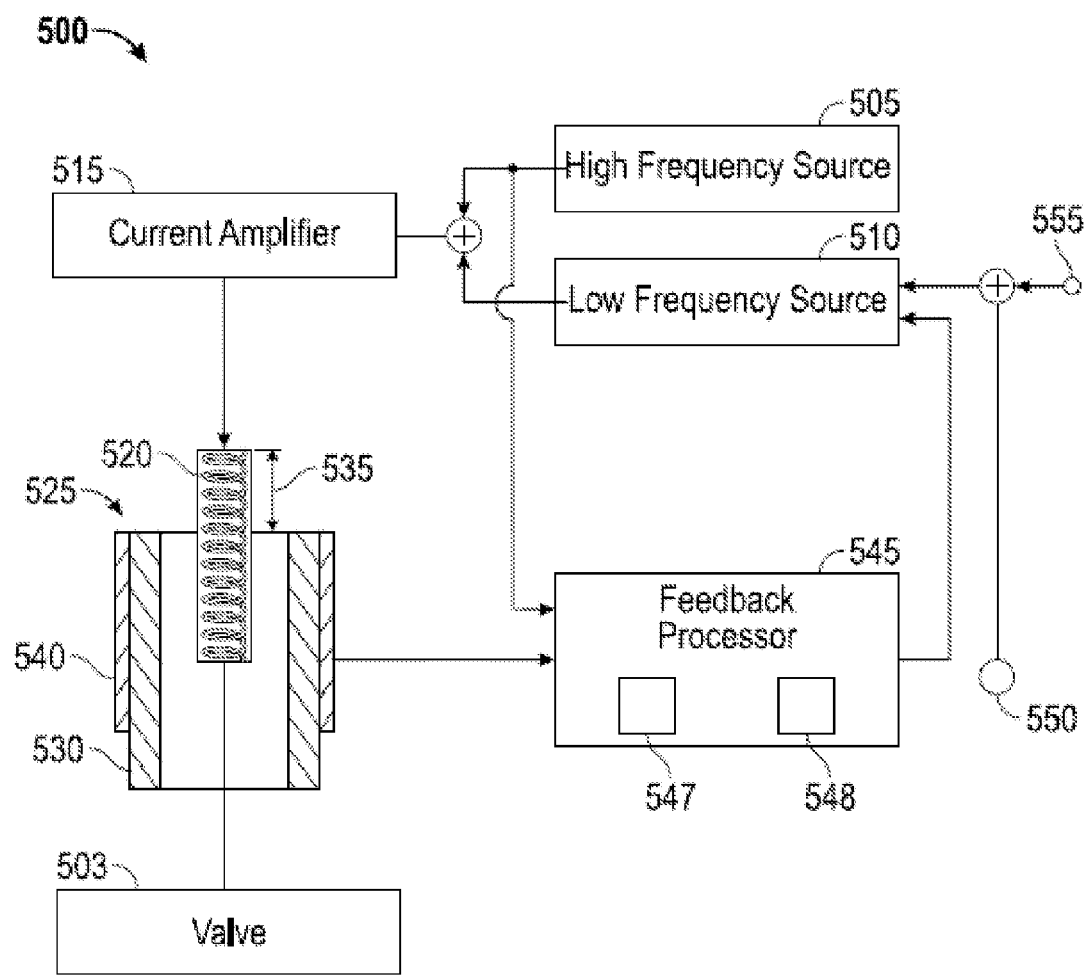
FIG. 5 illustrates an exemplary schematic arrangement of a control system according to certain aspects of the present disclosure.

FIG. 5 illustrates an exemplary schematic arrangement of a current control system 500 that illustrates some embodiments of a driver (e.g., the exhalation valve driver 440 of FIG. 4A or the inhalation valve driver 441 of FIG. 4B) operating to adjust a valve 503 (e.g., the exhalation valve 410 or the inhalation valve 411). In the illustrated system 500, a high frequency source 505 generates a signal having a high frequency, and a low frequency source 510 generates a signal having a low frequency. The high frequency signal and the low frequency signal are summed together, and the signal is amplified by a current amplifier 515. In some embodiments, the current amplifier 515 is a linear current output amplifier. The signal is then directed to a coil 520 (e.g., a force coil) that is configured to move at least partly within a fixed magnetic field 525. The fixed magnetic field 525 is produced by a magnetic field generator, e.g., at least one permanent magnet 530 or a separate coil (not shown).

The natural frequency of the coil 520 is such that the coil 520 responds to the low frequency component of the combined signal by movement within or in relation to the magnetic field, as illustrated by arrows 535. In some embodiments, the low frequency component is less than about 90% of the natural frequency of the coil 520. In some embodiments, the low frequency component is less than about 80% of the natural frequency of the coil 520, and in yet further embodiments, the low frequency component is less than about 50% of the natural frequency of the coil 520.

The high frequency component of the combined signal preferably has a negligible effect on the position of the coil 520 such that the position of the coil 520 within the magnetic field is controlled substantially by the low frequency component. For example, in some embodiments, the high frequency component is more than 50% greater than the natural frequency of the coil 520. In some embodiments, the high frequency component can be between 50% and about 200% greater than the natural frequency of the coil 520. In yet additional embodiments, the high frequency can be more than 200% greater than the natural frequency of the coil 520.

A detection coil 540, or a feedback coil, detects the high frequency component of the signal passing through the coil 520, and the detection coil 540 sends a signal to a high frequency feedback processor 545 that determines, based on the detection coil 540 signal, a position of the coil 520 within the magnetic field 525. In some embodiments, a magnitude of the high frequency signal detected by the detection coil 540 is used to determine the position of the coil 520 within the magnetic field 525. In some instances, the high frequency feedback processor 545 also determines a velocity of the coil 520 within the magnetic field 525 and the high frequency feedback processor 545 sends a signal to the low frequency source 510 for providing feedback on the position and/or velocity of the coil 520. In some embodiments, the high frequency feedback processor 545 includes a position circuit 547 and a velocity circuit 548.

The low frequency source 510 also receives input from a sensor (not shown) within a ventilator line relating to how an actual condition 550 (e.g., pressure or flow rate) within the ventilator line compares to a target condition 555 of the ventilator line. Based on (i) the input relating to the comparison of actual condition 550 and the target condition 555 and (ii) the input from the high frequency feedback processor 545 relating to the position of the coil 520 in relation to the magnetic field 525, the low frequency source 510 determines whether the low frequency signal should be modified to change the position of the coil 520 in relation to the magnetic field 525.

For example, if the actual condition 550 were determined to be outside of an acceptable range of values set by the target condition 555, the low frequency source 510 changes the low frequency signal to move the coil 520 within the magnetic field 525. The coil 520 is preferably coupled, directly (e.g., mechanically) or indirectly (e.g., magnetically), to a portion of the valve 503 that regulates flow through the valve 503. Accordingly, movement of the coil 520 moves the portion of the valve 503 and changes an amount of gas passing through the valve 503. As the amount of gas passing through the valve 503 changes, the detected condition within the ventilator line changes, and the actual condition 550 is detected and compared with the target condition 555.

In some embodiments, it is advantageous to maintain a positive pressure within the ventilator line. For example, when the ventilator line is an exhalation line, or exhalation pathway, from a patient, and it is desirable to maintain a positive pressure within the patient's lungs relative to a local atmospheric pressure (or ambient pressure), the target condition 555 may include a minimum threshold pressure. When the actual condition 550 is determined to drop below the threshold pressure, the low frequency source 510 may be configured to close the valve 503, such that substantially no gas from the exhalation line passes through the valve 503. The valve 503, in such instances, may remain closed until the actual condition 550 within the exhalation line increases above the threshold pressure, at which time, the low frequency source 510 receives inputs reflecting that the valve 503 should be opened, and the source 510 changes the low frequency signal to move the coil 520 to a position in relation to the magnetic field 525 that corresponds to an opening of the valve 503. In some instances, upon receiving a signal that the actual condition 550 is above the threshold pressure, the low frequency source 510 may produce a signal that maintains position of the coil 520, and therefore the valve 503, to further increase the actual pressure within the exhalation line.

In some embodiments, it is advantageous to regulate a flow rate within the ventilator line. For example, when the ventilator line is an inhalation line, or inhalation pathway, to a patient, and it is desirable to regulate the flow rate to reach a target volume of gas, the target condition 555 may include a threshold time of flow rate. When the actual condition 550 is determined to reach the threshold time of flow rate, the low frequency source 510 may be configured to close the valve 503, such that substantially no gas from the inhalation line passes through the valve 503. The valve 503, in such instances, may remain closed until the next cycle, at which time, the low frequency source 510 receives inputs reflecting that the valve 503 should be opened, and the source 510 changes the low frequency signal to move the coil 520 to a position in relation to the magnetic field 525 that corresponds to an opening of the valve 503. In some instances, upon receiving a signal that the actual condition 550 has not reached the threshold time of flow rate, the low frequency source 510 may produce a signal that maintains position of the coil 520, and therefore the valve 503, to maintain the flow rate through the inhalation line.

Figure 6A:
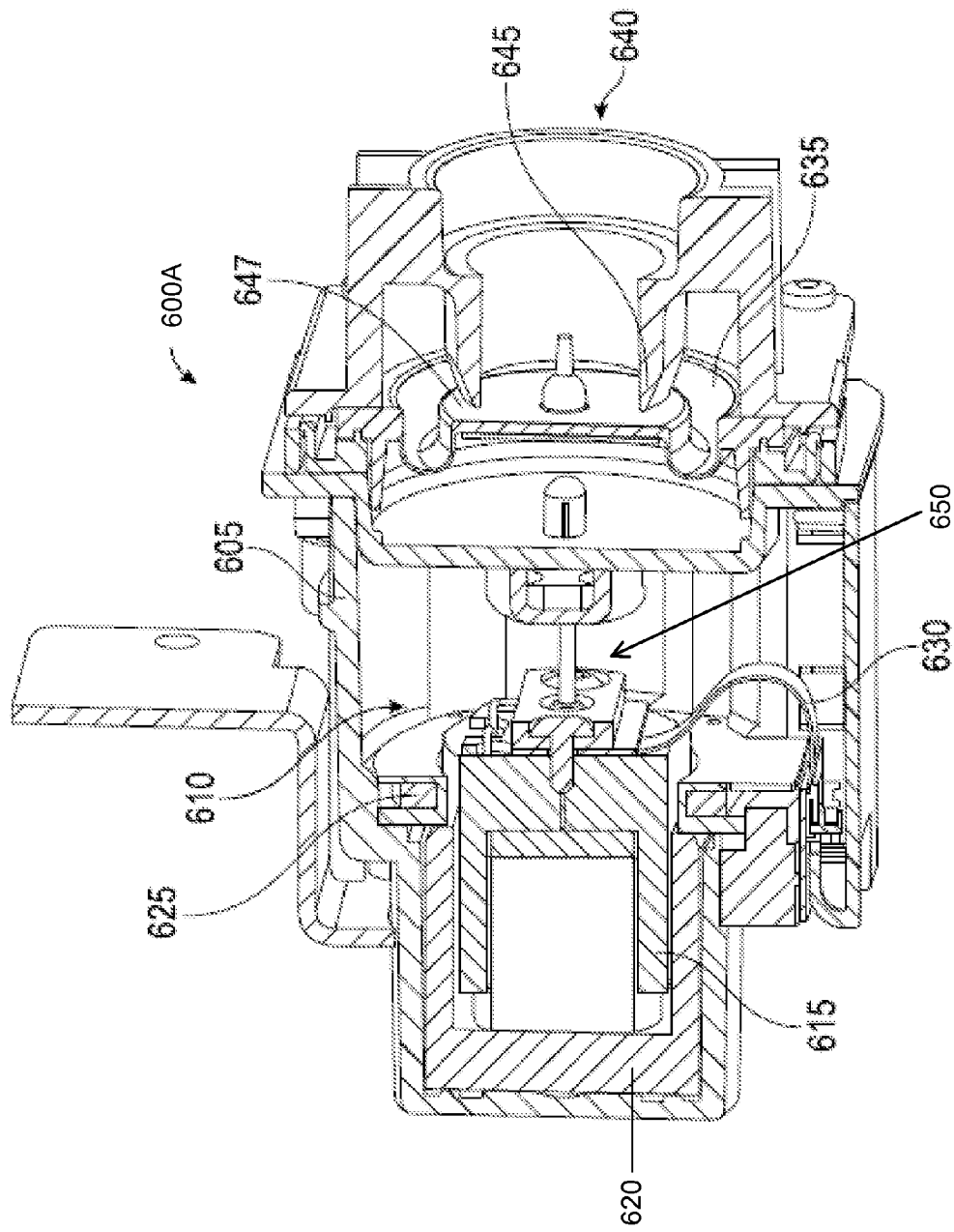
FIG. 6A is a cross sectional view of a flow valve according to certain aspects of the present disclosure.

FIG. 6A is an exemplary cross sectional view of the a valve 600A, which may be the exhalation valve 410 or the inhalation valve 411, and operates under the same or similar principles described above with respect to valve 503 depicted in FIG. 5. The illustrated valve 600A includes a housing 605 that defines an internal chamber 610. Disposed within the internal chamber 610 is a coil 615 that is positioned and axially movable within or in relation to a fixed magnetic field generator 620. An armature 650 has a pole piece and may include or be attached to the coil 615. Positioned about at least a portion of the magnetic field generator 620 is a sensor 625. In some embodiments, the sensor 625 is a detection coil that is configured to detect high frequency signals passing through the coil 615. The high frequency signals detected by the sensor 625 are used to determine a position of the coil 615 within or in relation to the magnetic field generator 620.

A signal is communicated from the sensor 625 regarding a position of the coil 615, and signals are directed to the coil 615 via a flexible communication cable 630. As the signals directed to the coil 615 cause the coil 615 to move within the internal chamber 610 in relation to the magnetic field, movement of the coil 615 affects positioning of a convoluted diaphragm 635 and poppet 647 or seal. The poppet 647 operates as a variable orifice of the valve 600. Positioning of the poppet 647 with respect to the seat 645 affects the amount of fluid that passes through a valve having an opening 640.

Movement of the coil 615 can change a position of the sensor 625 by being directly coupled to the poppet 647 and moving the poppet 647 toward or away from a seat 645, which defines the valve orifice as the gap between the poppet 647 and seat 645. For example, the armature 650 may be directly connected to the diaphragm 635 and/or the poppet 647. In some embodiments, movement of the coil 615 can change a position of the poppet 647 by being indirectly coupled to the poppet 647. For example, a portion of the coil 615 and a portion of the poppet 647 may be magnetically opposed or attracted to each other. In such embodiments, movement of the coil 615 thereby opposes or attracts the portion of the poppet 647. In a similar configuration to direct coupling, this indirect coupling can affect positioning of the poppet 647 in connection with the seat 645 of the valve without contact between the coil 615 and the poppet 647.

Although a diaphragm with a poppet is illustrated in FIG. 6A, other types of valve configurations may be used in connection with the described embodiments. For example, other valves that can be used include, but are not limited to, a flap valve, a rotating disk valve, a duck-billed valve, etc.

The valve 600A can also provide increased stability by damping the moving components of the valve 600A. As explained above, a velocity of the coil 615 can be determined by a processor (e.g., processor 430 or 431 or high frequency feedback processor 545), which can include a velocity circuit that calculates a change of position with respect to time. The velocity can then be used to determine the desired damping. With the assumption that the valve 600A functions as a second order system, the damped frequency response is greater than or equal to about 40 Hz, and the damping coefficient that yields an under-damped or critically damped valve assembly. In other embodiments, additional damping such as pneumatic viscous damping can be incorporated into the valve 600A to further tune the valve 600A to the specific application.

The valve 600A can include a "fail-safe" open feature in case of loss of electrical power, software control, or loss of all inlet gases. The valve 600A can also be configured to switch to the "fail-safe" open configuration when the ventilator 100 is turned off. On successful completion of power on checks, the ventilator 100 will close the valve 600A and normal ventilation can commence. During a ventilator 100 "fail-safe" open condition, the valve 600A, and other valves or ports will work in conjunction to (i) relieve pressure from the circuit down to ambient pressure conditions, (ii) allow ambient air to be available to the patient for breathing, and (iii) minimize re-breathing of gases.

Figure 6B:
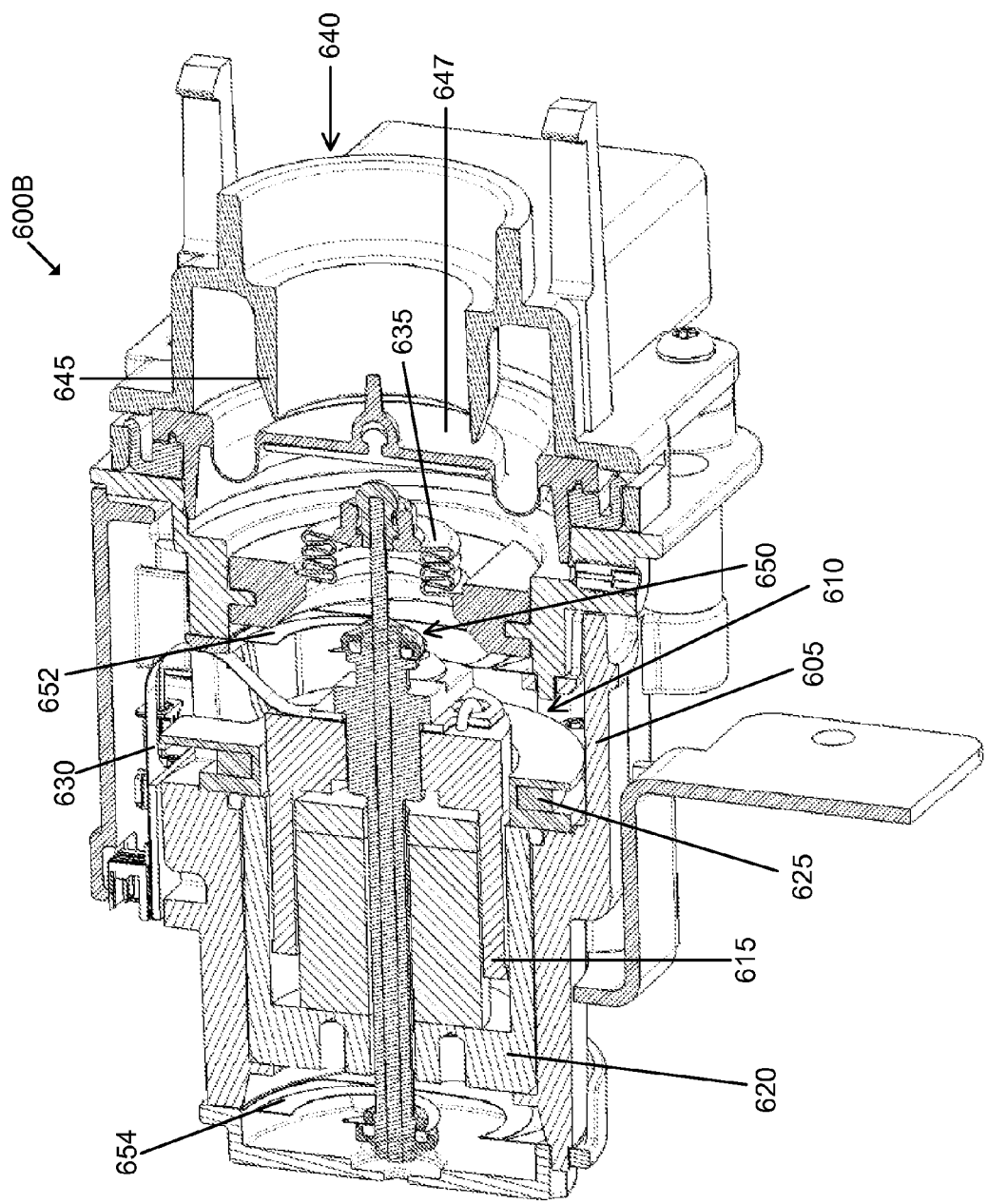
FIG. 6B is a cross sectional view of a flow valve according to certain aspects of the present disclosure.

FIG. 6B illustrates a valve 600B, which may be another implementation of the valve 600A. The valve 600B may comprise similar components as the valve 600A. In addition, the valve 600B comprises a front flat spring 652, and a rear flat spring 654. The front flat spring 652 and the rear flat spring 654 provide mechanical or structural support for the armature 650. In other implementations, the armature 650 may be supported by other structures, such as bearings.

Figure 7:
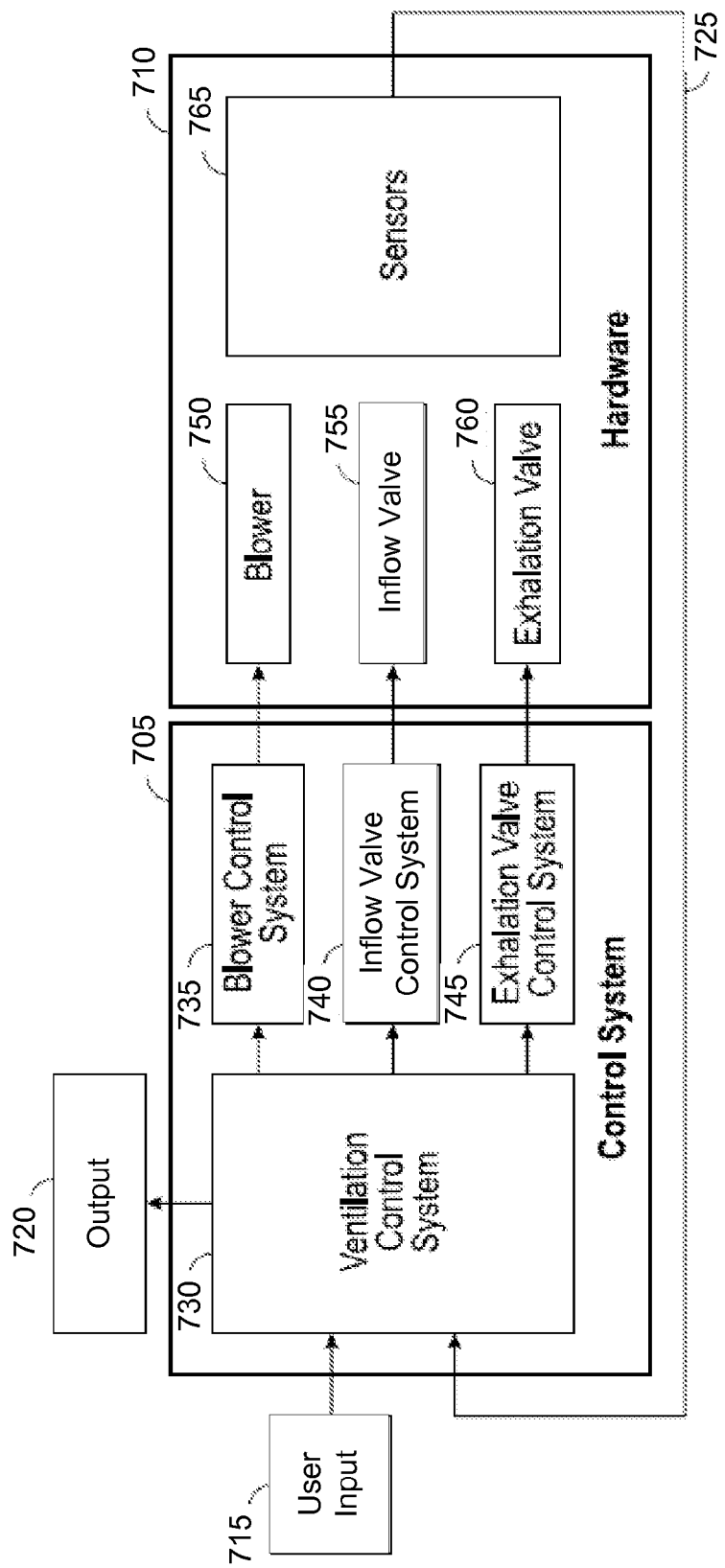
FIG. 7 is a schematic representation of a ventilator according to certain aspects of the present disclosure.

FIG. 7 illustrates a schematic depiction of another implementation of the ventilator 100 having a control system 705, system hardware 710, user input 715, output 720, and feedback 725. The control system 705 includes a ventilation control system 730 that receives user input 715. The control system 705 includes hardware control systems that control respective hardware components of the ventilator 100. For example, the hardware control systems may include a blower control system 735, an inflow valve control system 740, and an exhalation valve control system 745. The blower control system 735 controls a respective blower 750, the inflow valve control system 740 controls a respective inflow valve 755, and the exhalation valve control system 745 controls a respective exhalation valve 760.

The system hardware 710 includes sensors 765 that detect information from the system hardware 710, for example, the blower 750, the inflow valve 755, and the exhalation valve 760. The sensors 765 produce one or more feedback signals 725 that are received by the ventilation control system 730. The ventilation control system 730 receives the feedback control signals 725 and the user input 715 and sends information to an output 720. The output 720 can include, for example, monitoring information and alarms.

The inflow valve control system 740 may be similar to and operate similarly to the exhalation valve control system 745, which may correspond to the feedback system 400 in FIG. 4 or the current control system 500 in FIG. 5. The inflow valve 755 may also be similar to and operate similarly to the exhalation valve 760, which may correspond to the exhalation valve 410 in FIGS. 4 and 6, or the valve 503 in FIG. 5. Although labeled as inflow valve 755, the inflow valve 755 may be any front end valve before the patient in a gas flow. The exhalation valve 760 may be any back end valve behind the patient in a gas flow.

In FIG. 3, a flow cassette is used, whereas in FIG. 7, a valve control system is used instead. A flow cassette may include a pressure measurement device for an inlet gas, which measures pressure differential to determine flow measurement. The flow cassette may also include another valve tracker that drives the flow control valve of the flow cassette. Thus, a flow cassette provides flow measurement and flow control.

The valve control systems described herein provide flow control through the variable valve opening, but also provide flow measurement. The flow measurement can be derived from the position of the force coil or drive coil. Thus, the valve control systems also provide flow measurement and flow control, similar to flow cassettes. However, flow cassettes may be cost prohibitive for certain applications. For example, in certain applications, a ventilator system with valve control systems may be less expensive to produce than a ventilator system with one or more flow cassettes. The valve control systems may be different sizes, for example one quarter of the size of the other, as needed. The two valve control systems can work together, with one for inspiration and one for exhalation. For example, the inflow valve 755 may be open and regulated until an appropriate volume of gas has flowed to the patient. The inflow valve 755 will then close, and the exhalation valve 760 will open, and regulated until an appropriate volume of gas has been exhaled by the patient.

More particularly, gas is connected to the inflow valve 755 which starts closed, building up high pressure. The inflow valve control system 740 commands the inflow valve 755 to open, allowing the flow through to the patient. When inspiration starts, the exhalation valve 760 is closed. The inflow valve control system 740 determines when to close the inflow valve 755 based on a flow control or a pressure control. When the inflow valve 755 is closed, the exhalation valve control system 745 commands the exhalation valve 760 to open, allowing the patient to breathe out. The inflow valve 755 is directed to open, and the cycle repeats. Flow control may be calculated by sampling, for instance, the pressure every millisecond to make adjustments. Based on the position of the drive coil, the pressure can be calculated. The pressure is continuously monitored to adjust the position of the drive coil until a target flow is reached. The calculations may factor in ambient pressure, gas composition, gas temperature changes, downstream pressure changes, inlet pressure changes, etc. The calculations may further correct for standard conditions. By continuously monitoring pressure and adjusting the position of the drive coil, the exhalation valve 760 allows the patient to exhale without difficulty.

Although the flow control devices described herein may be used in connection CPAP therapy, other embodiments, particularly embodiments used on the front end of the ventilator, are not limited to CPAP therapy. The flow control devices described herein may be utilized at any point along a flow path of a ventilator, respirator, or other similar device. In addition, the flow control devices may be used in other fluid devices, particularly fluid devices which measure and/or regulate fluid flow, and are not limited to respiration.

Figure 8:
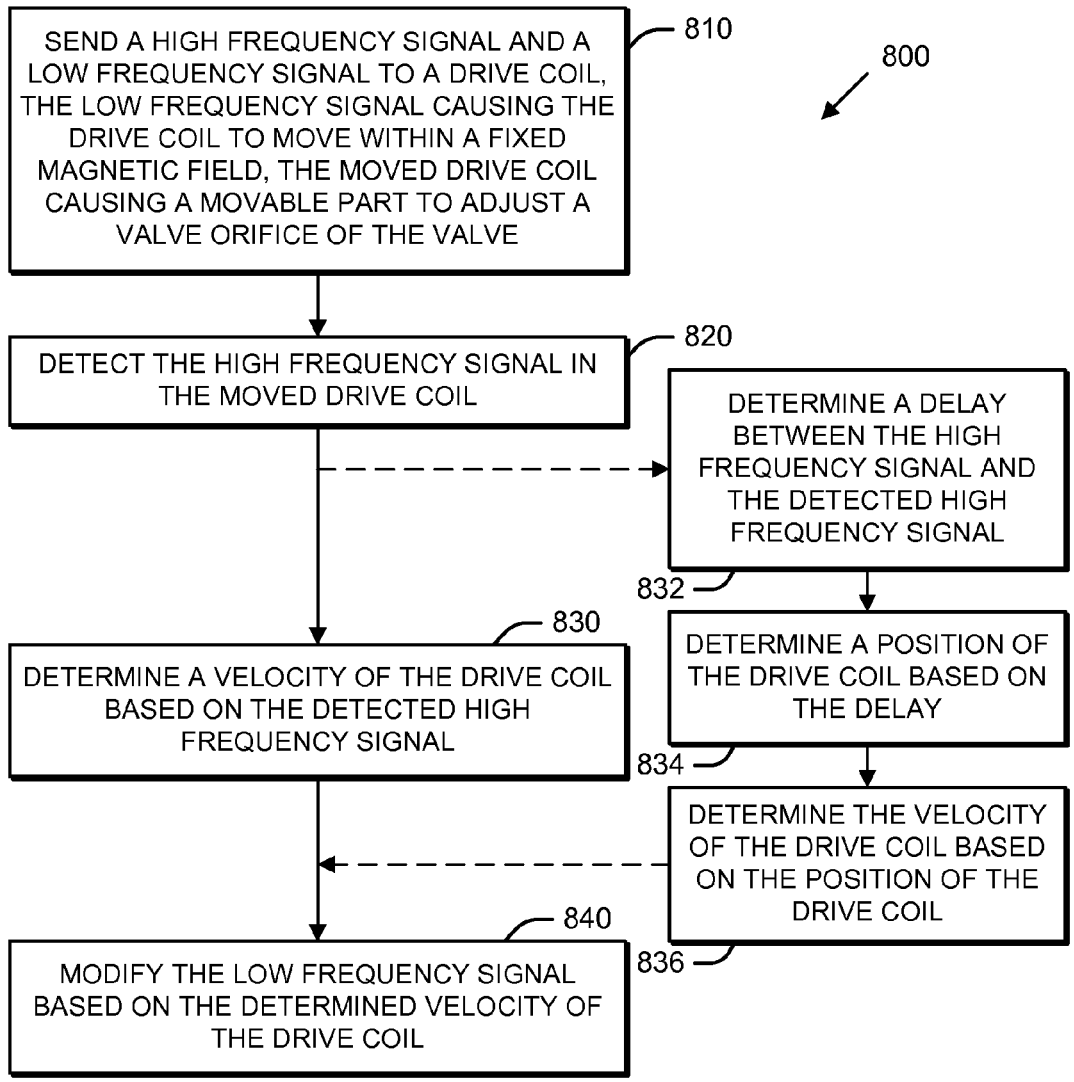
FIG. 8 shows a flowchart of a process for controlling a flow valve according to certain aspects of the present disclosure.

FIG. 8 shows a flowchart 800 of controlling a flow valve, such as the valve 503. At block 810, a high frequency signal and a low frequency signal is sent to a drive coil, such as the coil 615. The low frequency signal causes the drive coil to move within a fixed magnetic field, such as the fixed magnetic field generator 620. The moved drive coil causes a movable part, such as the poppet 647 or seal, to adjust a valve orifice of the valve, such as the opening 640. At block 820, the high frequency signal in the moved drive coil is detected. At block 830, a velocity of the drive coil is determined based on the detected high frequency signal. At block 840, the low frequency signal is modified based on the determined velocity of the drive coil. For example, the velocity signal may be injected into the low frequency source for the purpose of dampening.

Figure 9:
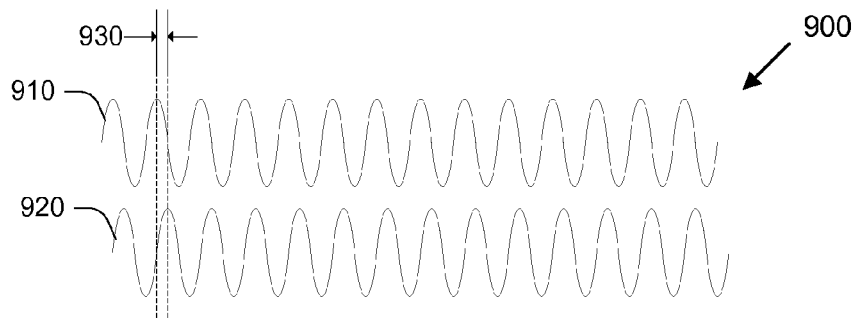
FIG. 9 illustrates high frequency signals according to certain aspects of the present disclosure.

The block 830 may be expanded into several operations, denoted by the dotted lines in FIG. 8. At block 832, a delay between the high frequency signal and the detected high frequency signal may be determined. FIG. 9 shows a sample space 900. A high frequency signal 910, which may be a high frequency current from the high frequency source 505, is compared to a detected high frequency signal 920, which may be a high frequency current detected in the drive coil after the drive coil moves. A delay 930 between the signals may be proportional to the position of the drive coil. Thus, at block 834, the position of the drive coil is determined based on the delay. At block 836, the velocity of the drive coil is determined based on the position of the drive coil. With the velocity determined at block 836, at block 840, the low frequency signal may be modified based on the determined velocity of the drive coil to, for example, control dampening of the drive coil.

The previous description is provided to enable any person skilled in the art to practice the various aspects described herein. While the foregoing has described what are considered to be the best mode and/or other examples, it is understood that various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the terms "a set" and "some" refer to one or more. Pronouns in the masculine (e.g., his) include the feminine and neuter gender (e.g., her and its) and vice versa. Headings and subheadings, if any, are used for convenience only and do not limit the invention.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

A phrase such as an "aspect" does not imply that such aspect is essential to the subject technology or that such aspect applies to all configurations of the subject technology. A disclosure relating to an aspect may apply to all configurations, or one or more configurations. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. A phrase such an embodiment may refer to one or more embodiments and vice versa.

The word "exemplary" is used herein to mean "serving as an example or illustration." Any aspect or design described herein as "exemplary" is not necessarily to be construed as preferred or advantageous over other aspects or designs.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used in the description or the claims, such term is intended to be inclusive in a manner similar to the term "comprise" as "comprise" is interpreted when employed as a transitional word in a claim.

This specification describes example aspects of the subject technology, which may include at least the following concepts:

Concept 1. A flow control device comprising: a high frequency source configured to generate a high frequency signal; a low frequency source configured to generate a low frequency signal; a fixed magnetic field; a drive coil configured to move within the fixed magnetic field in response to the low frequency signal and configured to receive the high frequency signal; a detection coil adjacent the drive coil and configured to detect the high frequency signal in the drive coil, the detected high frequency signal corresponding to a position of the drive coil; a processor coupled to the high frequency source and the low frequency source and configured to receive the detected high frequency signal from the detection coil; a seal configured to move based on the position of the drive coil; and a valve orifice defining a valve seat and a variable opening, the variable opening being adjustable based on a position of the seal relative to the valve seat.

Concept 2. The flow control device of Concept 1, wherein the processor is further configured to calculate the position of the drive coil based on a delay between the high frequency signal and the detected high frequency signal, and wherein the delay is proportional to the position of the drive coil.

Concept 3. The flow control device of Concept 2, wherein the processor is further configured to calculate a velocity of the drive coil based on the calculated position of the drive coil.

Concept 4. The flow control device of Concept 3, wherein the processor is further configured to modify the low frequency signal based on the calculated velocity of the drive coil.

Concept 5. The flow control device of Concept 1, wherein the seal is mechanically coupled to the drive coil.

Concept 6. The flow control device of Concept 1, wherein the seal is configured to engage the valve seat to close the variable opening.

Concept 7. The flow control device of Concept 1, wherein the detection coil surrounds the drive coil.

Concept 8. The flow control device of Concept 1, further comprising a chamber, wherein the fixed magnetic field, the drive coil, and the detection coil are positioned within the chamber.

Concept 9. A ventilator system comprising: a first valve connected to a supply channel and comprising: a first high frequency source configured to generate a first high frequency signal; a first low frequency source configured to generate a first low frequency signal; a first fixed magnetic field; a first drive coil configured to move within the first fixed magnetic field in response to the first low frequency signal and configured to receive the first high frequency signal; a first detection coil adjacent the first drive coil and configured to detect the first high frequency signal in the drive coil, the detected first high frequency signal corresponding to a position of the first drive coil; a first processor coupled to the first high frequency source and the first low frequency source and configured to receive the detected first high frequency signal from the first detection coil; a first seal configured to move based on the position of the first drive coil; and a variable first valve orifice defining a first valve seat, the first valve orifice being adjustable based on a position of the first seal relative to the first valve seat.

Concept 10. The ventilator system of Concept 9, wherein the first processor further comprises a first position circuit configured to calculate the position of the first drive coil based on a delay between the first high frequency signal and the detected first high frequency signal, and wherein the delay is proportional to the position of the first drive coil.

Concept 11. The ventilator system of Concept 10, wherein the first processor further comprises a first velocity circuit configured to calculate a velocity of the first drive coil based on the calculated position of the first drive coil.

Concept 12. The ventilator system of Concept 11, wherein the first processor is further configured to modify the first low frequency signal based on the calculated velocity of the first drive coil.

Concept 13. The ventilator system of Concept 12, wherein the first processor is further configured to continuously modify the first low frequency signal.

Concept 14. The ventilator system of Concept 9, further comprising a second valve connected to an exhaust channel, the second valve comprising: a second high frequency source configured to generate a second high frequency signal; a second low frequency source configured to generate a second low frequency signal; a second fixed magnetic field; a second drive coil configured to move within the second fixed magnetic field in response to the second low frequency signal and configured to receive the second high frequency signal; a second detection coil adjacent the second drive coil and configured to detect the second high frequency signal in the second drive coil, the detected second high frequency signal corresponding to a position of the second drive coil; a second processor coupled to the second high frequency source and the second low frequency source and configured to receive the detected second high frequency signal from the second detection coil; a second seat configured to move based on the position of the second drive coil; and a second valve orifice defining a second valve seat, the second valve orifice being adjustable based on a position of the second seal relative to the first valve seat.

Concept 15. The ventilator system of Concept 14, wherein the second processor further comprises a second position circuit configured to calculate the position of the second drive coil based on a delay between the second high frequency signal and the detected second high frequency signal, and wherein the delay is proportional to the position of the second drive coil.

Concept 16. The ventilator system of Concept 15, wherein the second processor further comprises a second velocity circuit configured to calculate a velocity of the second drive coil based on the calculated position of the second drive coil.

Concept 17. The ventilator system of Concept 16, wherein the second processor is further configured to modify the second low frequency signal based on the calculated velocity of the second drive coil.

Concept 18. The ventilator system of Concept 14, wherein the first processor and the second processor are configured to alternate in opening the first valve orifice and the second valve orifice, respectively.

Concept 19. A method for adjusting a valve, the method comprising: sending a high frequency signal and a low frequency signal to a drive coil, the low frequency signal causing the drive coil to move within a fixed magnetic field, the drive coil causing a seal to adjust a variable valve orifice of the valve; detecting the high frequency signal in the drive coil; determining a velocity of the drive coil based on the detected high frequency signal; and modifying the low frequency signal based on the determined velocity of the drive coil.

Concept 20. The method of Concept 19, wherein determining the velocity further comprises: determining a delay between the high frequency signal and the detected high frequency signal; determining a position of the drive coil based on the delay; and determining a change of position of the drive coil over a change in time

What is claimed is:

1. A flow control device comprising:
   a high frequency source configured to generate a high frequency signal;
   a low frequency source configured to generate a low frequency signal;
   a fixed magnetic field;
   a drive coil configured to move within the fixed magnetic field in response to the low frequency signal and configured to receive the high frequency signal;
   a detection coil adjacent the drive coil and configured to detect the high frequency signal in the drive coil, the detected high frequency signal corresponding to a position of the drive coil;
   a processor coupled to the high frequency source and the low frequency source and configured to receive the detected high frequency signal from the detection coil, and calculate the position of the drive coil based on a delay between the high frequency signal and the detected high frequency signal, wherein the delay is proportional to the position of the drive coil;
   a seal configured to move based on the position of the drive coil; and
   a valve orifice defining a valve seat and a variable opening, the variable opening being adjustable based on a position of the seal relative to the valve seat.

2. The flow control device of claim 1, wherein the seal is mechanically coupled to the drive coil.

3. The flow control device of claim 1, wherein the seal is configured to engage the valve seat to close the variable opening.

4. The flow control device of claim 1, wherein the detection coil surrounds the drive coil.

5. The flow control device of claim 1, further comprising a chamber, wherein the fixed magnetic field, the drive coil, and the detection coil are positioned within the chamber.

6. The flow control device of claim 1, wherein the processor is further configured to calculate a velocity of the drive coil based on the calculated position of the drive coil.

7. The flow control device of claim 6, wherein the processor is further configured to modify the low frequency signal based on the calculated velocity of the drive coil.

8. A ventilator system comprising:
   a first valve connected to a supply channel and comprising:
     a first high frequency source configured to generate a first high frequency signal;
     a first low frequency source configured to generate a first low frequency signal;
     a first fixed magnetic field;
     a first drive coil configured to move within the first fixed magnetic field in response to the first low frequency signal and configured to receive the first high frequency signal;
     a first detection coil adjacent the first drive coil and configured to detect the first high frequency signal in the first drive coil, the detected first high frequency signal corresponding to a position of the first drive coil;
     a first processor coupled to the first high frequency source and the first low frequency source and configured to receive the detected first high frequency signal from the first detection coil, the first processor including a first position circuit configured to calculate the position of the first drive coil based on a delay between the first high frequency signal and the detected first high frequency signal, the delay being proportional to the position of the first drive coil;
     a first seal configured to move based on the position of the first drive coil; and
     a variable first valve orifice defining a first valve seat, the first valve orifice being adjustable based on a position of the first seal relative to the first valve seat.

9. The ventilator system of claim 8, wherein the first processor further comprises a first velocity circuit configured to calculate a velocity of the first drive coil based on the calculated position of the first drive coil.

10. The ventilator system of claim 9, wherein the first processor is further configured to modify the first low frequency signal based on the calculated velocity of the first drive coil.

11. The ventilator system of claim 10, wherein the first processor is further configured to continuously modify the first low frequency signal.

12. The ventilator system of claim 8, further comprising a second valve connected to an exhaust channel, the second valve comprising:
   a second high frequency source configured to generate a second high frequency signal;
   a second low frequency source configured to generate a second low frequency signal;
   a second fixed magnetic field;
   a second drive coil configured to move within the second fixed magnetic field in response to the second low frequency signal and configured to receive the second high frequency signal;
   a second detection coil adjacent the second drive coil and configured to detect the second high frequency signal in the second drive coil, the detected second high frequency signal corresponding to a position of the second drive coil;

a second processor coupled to the second high frequency source and the second low frequency source and configured to receive the detected second high frequency signal from the second detection coil;

a second seal configured to move based on the position of the second drive coil; and a second valve orifice defining a second valve seat, the second valve orifice being adjustable based on a position of the second seal relative to the first valve seat.

13. The ventilator system of claim 12, wherein the first processor and the second processor are configured to alternate in opening the first valve orifice and the second valve orifice, respectively.

14. The ventilator system of claim 12, wherein the second processor further comprises a second position circuit configured to calculate the position of the second drive coil based on a delay between the second high frequency signal and the detected second high frequency signal, and wherein the delay is proportional to the position of the second drive coil.

15. The ventilator system of claim 14, wherein the second processor further comprises a second velocity circuit configured to calculate a velocity of the second drive coil based on the calculated position of the second drive coil.

16. The ventilator system of claim 15, wherein the second processor is further configured to modify the second low frequency signal based on the calculated velocity of the second drive coil.

17. A method for adjusting a valve, the method comprising:

sending a high frequency signal and a low frequency signal to a drive coil, the low frequency signal causing the drive coil to move within a fixed magnetic field, the drive coil causing a seal to adjust a variable valve orifice of the valve;

detecting the high frequency signal in the drive coil;

determining a delay between the high frequency signal and the detected high frequency signal;

determining a position of the drive coil based on the delay;

determining a velocity of the drive coil based on the detected high frequency signal; and modifying the low frequency signal based on the determined velocity of the drive coil.

18. The method of claim 17, wherein determining the velocity further comprises determining a change of position of the drive coil over a change in time.

* * * * *